United States Patent [19]

Cölln et al.

[11] 4,127,401
[45] Nov. 28, 1978

[54] AMINOMETHANEPHOSPHONIC ACID COMPOUNDS CONTAINING PLANT-GROWTH REGULANT COMPOSITIONS

[75] Inventors: Reimer Cölln, Wuppertal; Klaus Lürssen, Grosskönigsdorf, both of Germany

[73] Assignee: Bayer Aktiengesellschaft, Leverkusen, Germany

[21] Appl. No.: 770,349

[22] Filed: Feb. 22, 1977

Related U.S. Application Data

[63] Continuation of Ser. No. 660,542, Feb. 23, 1976, abandoned, which is a continuation of Ser. No. 478,132, Jun. 10, 1974, abandoned.

[30] Foreign Application Priority Data

Jun. 19, 1973 [DE] Fed. Rep. of Germany ....... 2331187

[51] Int. Cl.² ............................................. A01N 9/36
[52] U.S. Cl. ......................................... 71/76; 71/86
[58] Field of Search .................................. 71/86, 76

[56] References Cited

U.S. PATENT DOCUMENTS 3,894,861  7/1975  Hartman ................................. 71/76

OTHER PUBLICATIONS

Ryzhkov et al., Chem. Abst., vol. 49, 3404a.

*Primary Examiner*—Catherine L. Mills
*Attorney, Agent, or Firm*—Sprung, Felfe, Horn, Lynch & Kramer

[57] ABSTRACT

Plant-growth regulating compositions and methods having strong effects on plant growth, containing an aminomethanephosphonic acid composed of the formula

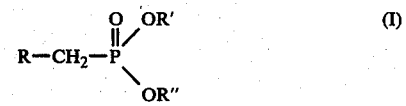

in which
R is an $NH_2$ group or an $-NH^{\oplus}_3 X^{\ominus}$ radical wherein $X^{\ominus}$ is one equivalent of an anion of an organic or inorganic acid, and
R' and R", which may be identical or different, are each alkyl of from 1 to 6 carbon atoms, one equivalent of an alkali metal or alkaline earth metal cation, one equivalent of a protonized nitrogen base or of a compound which contains an $N^{\oplus}H_3$ group, or hydrogen, provided that R' and R" can simultaneously be hydrogen only if R is an $-N^{\oplus}H_3 X^{\ominus}$ radical.

3 Claims, No Drawings

AMINOMETHANEPHOSPHONIC ACID COMPOUNDS CONTAINING PLANT-GROWTH REGULANT COMPOSITIONS

This is a continuation of application Ser. No. 660,542 filed Feb. 23, 1976, which, in turn, is a continuation of application Ser. No. 478,132, filed June 10, 1974 (both now abandoned).

The present invention relates to plant-growth regulant compositions and to methods of regulating plant-growth. More specifically, the compositions contain certain aminomethanephosphonic acid compounds.

The use of certain aminomethanephosphonic acid derivatives as additives to antibiotics or as intermediates for the preparation of phosphonodiazomethane derivatives or of aminomethanephosphonic acid is known (see Sinetezy Org. Soedinii Shomik 2, 12–15 (1954); Justus Liebigs Ann. Chem. 748 (1971) 207–210; Chem. Abstr. 45 (1951) 8444; and Australian Pat. No. 34,471/63).

It is also known that certain 2-halogenoethyl-ammonium halides, especially (2-chloroethyl)-trimethyl-ammonium chloride, display plant-growth-regulating properties (see U.S. Pat. No. 3,156,554). Thus (2-chloroethyl)-trimethyl-ammonium chloride, in particular, can be used to inhibit the vegetative growth of cereals, for example wheat and barley. However, the action of this compound is not always satisfactory if low concentrations are used.

It has now been found that the aminomethanephosphonic acid derivatives of the formula

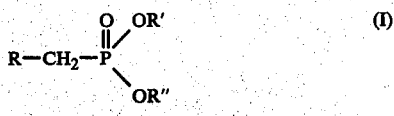

in which

R is an $NH_2$ group or an $-NH^{\oplus}_3 X^{\ominus}$ radical wherein $X^{\ominus}$ is one equivalent of an anion of an organic or inorganic acid, and R' and R", which may be identical or different, are each alkyl or from 1 to 6 carbon atoms, one equivalent of an alkali metal or alkaline earth metal cation, one equivalent of a protonized nitrogen base or of a compound which contains an $N^{\oplus}H_3$ group, or hydrogen, provided that R' and R" can simultaneously be hydrogen only if R is an $-N^{\oplus}H_3 X^{\ominus}$ radical, display strong plant-growth-regulating properties.

The present invention thus provides a plant-growth-regulating composition containing as active ingredient a compound of the formula (I) above in admixture with a solid or liquefied gaseous diluent or carrier or in admixture with a liquid diluent or carrier containing a surface-active agent.

The present invention also provides a method of regulating the growth of plants, which comprises applying to the plants or a plant habitat a compound of the formula (I) above alone or in the form of a composition containing as active ingredient a compound of the formula (I) above in admixture with a diluent or carrier.

Surprisingly, the aminomethanephosphonic acid derivatives which can be used according to the invention display a substantially greater plant-growth-regulating action than the known compound (2-chloroethyl)-trimethyl-ammonium chloride, which is chemically the nearest active compound of the same type of action. A point to be singled out is that the aminomethanephosphonic acid derivatives are substantially better suited to inhibiting the vegetative growth of cereals, especially wheat and barley, than is (2-chloroethyl)-trimethyl-ammonium chloride. An inhibition of the vegetative growth of cereals is of advantage because this produces shorter but thicker stalks, which reduces the danger of the plants kinking (falling-over) before harvesting. The present invention thus represents a valuable enrichment of the art.

Preferably, R is an $NH_2$ group or an $-N^{\oplus}H_3 X^{\ominus}$ radical in which $X^{\ominus}$ is one equivalent of an anion of an optionally substituted carboxylic acid, of a hydrogen halide acid, of a halogen-oxygen acid, of nitric acid or of an acid containing sulfur, such as sulfuric acid or a sulfonic acid; and R' and R" are each hydrogen (subject to the above proviso), straight-chain or branched alkyl of from 1 to 4 carbon atoms, one equivalent of a sodium, potassium, calcium or magnesium cation, one equivalent of a protonized nitrogen base, such as ammonia, monoalkylamines, dialkylamines, trialkylamines, cycloalkylamines, ethylenediamine, pyrrolidine, imidazole, piperidine, morpholine or aniline, one equivalent of the protonized form of a hydrazine, hydroxylamine, aminoalcohol, amidine or Schiff's base, or one equivalent of an aminoacid protonized at the $NH_2$ group, such as glycine, or of a corresponding protonized aminoacid ester, such as glycine ethyl ester.

The following may be mentioned as examples of the compounds which can be used according to the invention: O-methylaminomethanephosphonic acid monoester, O-ethyl-aminomethanephosphonic acid monoester, O-n-propyl-aminomethanephosphonic acid monoester, O-isopropyl-aminomethanephosphonic acid monoester, O-n-butyl-aminomethanephosphonic acid monoester, 0-isobutyl-aminomethanephosphonic acid monoester, O-sec.-butyl-aminomethanephosphonic acid monoester, O-tert.-butyl-aminomethanephosphonic acid monoester, and also the sodium, potassium, ammonium, calcium, magnesium, monomethylammonium, dimethylammonium, monoethylammonium, diethylammonium and mono-tert.-butylammonium mono-salts of these O-alkyl-aminomethanephosphonic acid monoesters, as well as their mono-salts with pyrrolidine, imidazole, piperidine, morpholine, glycine, glycine ethyl ester, aniline, hydrazine, hydroxylamine, ethanolamine and benzalaniline, as well as, O,O-dimethyl-aminomethanesphosphonic acid diester, O,O-diethyl-aminomethanephosphonic acid diester, O,O-di-n-propyl-aminomethanephosphonic acid diester, O,O-di-isopropylaminomethanephosphonic acid diester, O,O-di-n-butylaminomethanephosphonic acid diester, O,O-di-isobutyl-aminomethanephosphonic acid diester, O,O-di-sec.-butyl-aminomethanephosphonic acid diester, O,O-di-tert.-butyl-aminomethanephosphonic acid diester, as well as potassium aminomethanephosphonate, sodium aminomethanephosphonate, calcium aminomethanephosphonate, magnesium aminomethanephosphonate, ammonium aminomethanephosphonate, methylamine aminomethanephosphonate, dimethylamine, aminomethanephosphonate trimethylamine aminomethanephosphonate, ethylamine aminomethanephosphonate, diethylamine aminomethanephosphonate, triethylamine aminomethanephosphonate, tert.-butylamine aminomethanephosphonate, pyrrolidine aminomethanephosphonate, imidazole aminomethanephosphonate, piperidine aminomethanephosphonate, morpholine aminomethanephosphonate, glycine aminomethanephosphonate, glycine ester aminomethanephosphonate, hydrazine aminomethanephosphonate, aniline aminomethanephosphonate, amidine aminomethanephosphonate, hydroxylamine aminomethanephosphonate cyclohexylamine aminomethanephosphonate, 2-aminoethanol aminomethanephosphonate, the corresponding di-salts and also O,O-dimethyl-ammonio-methyl-phosphonic acid chloride, ammonio-methyl-phosphonic acid bromide, di-(ammonio-methyl-phosphonic acid) sulfate, ammonio-methyl-phosphonic acid methylsulfonate, ammonio-methyl-phosphonic acid nitrate, ammonio-methyl-phosphonic acid acetate, ammonio-methyl-phosphonic acid dichloroacetate and ammonio-methyl-phosphonic acid trichloroacetate.

A number of the compounds to be used according to the invention are known as, for example, in the case of O,O-diethylaminomethanephosphonic acid diester, O-ethyl-aminomethanephosphonic acid monoester and its aniline salt (see Sinetezy Org. Soedinii Sbornik 2, 12–14 (1954); Justus Liebigs Ann. Chem. 748, 207–210 (1971); Chemical Abstracts 45, 8444 (1951); and Australian Pat. Spec. No. 34,471/63). However, their use as plant-growth regulators is new.

Some of the compounds which can be used according to the invention have not hitherto been described in the literature but can be prepared in a simple manner according to known processes.

Thus, for example, the alkali metal salts and ammonium salts of aminomethanephosphonic acid and their salts with nitrogen bases are obtained by adding 1 or 2 equivalents of base to a suspension of aminomethanephosphonic acid in distilled water. To isolate the reaction products, the reaction solution is evaporated in vacuo at 70° C and the residue which remains is left for some time at this temperature in vacuo.

The alkaline earth metal salts of aminomethanephosphonic acid are appropriately prepared by adding an equivalent amount of an alkaline earth metal salt solution to the aqueous solution of an alkali metal salt of aminomethanephosphonic acid. The desired products, which precipitate as solids in the course of the reaction, can be isolated by simple filtration.

The salts of the monoesters of aminomethanephosphonic acid are prepared in principle in the same manner as the salts of aminomethanephosphonic acid. However, instead of the free aminomethanephosphonic acid an appropriate monoester of this acid serves as the starting material.

The compounds of the formula (I) in which R represents an $-N^{\oplus}H_3X^{\ominus}$ radical, are obtainable by addition of a sufficiently strong acid to aqueous solutions or suspensions of the free aminomethanephosphonic acid or its monoesters or diesters. The compounds can be isolated by evaporating off the excess solvent in vacuo at 70° C.

Aminomethanephosphonic acid, required as a starting material in the preparation of the compounds which can be used according to the invention, is also known, as are the esters of aminomethanephosphonic acid which also serve as starting materials (see Chemical Abstracts 45, 8444 (1951)). The other compounds employed as starting materials are generally known.

The preparation of the compounds to be used according to this invention is illustrated in the following Example.

EXAMPLE 1

Preparation of Sodium Aminomethanephosphonate

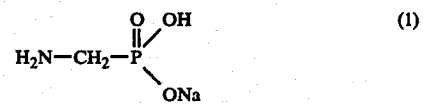

A solution of 4 g (0.1 mole) of sodium hydroxide in 20 ml of distilled water was added to a suspension of 11.11 g (0.1 mole) of aminomethanephosphonic acid in 50 ml of distilled water. Hereupon, salt formation occurred and a clear solution resulted. The solution was then evaporated to dryness in vacuo at a bath temperature of 70° C. The residue which hereupon remained was comminuted and left for a further 30 to 60 minutes in vacuo at 70° C. In this way, 6.65 g (100% of theory) of sodium aminomethanephosphonate were obtained, which decomposed on heating at 320° C.

The following compounds were prepared by methods analogous to that in Example 1:

| Ex. No. | Compound | Content of water of crystallisation (in moles) | Nitrogen content in % calculated | Nitrogen content in % found | Behaviour on heating |
|---|---|---|---|---|---|
| 2 | H₂N—CH₂—P(=O)(OH)(OX) | 2.5 | 7.2 | 7.3 | H₂O given off from 100° C; decomposition at 310° C |
| 3 | H₂N—CH₂—P(=O)(OH)(ONH₄) | 0 | | | Decomposition from 270° C |
| 4 | H₂N—CH₂—P(=O)(OH)(O⁻ NH₃⁺—CH₃) | 0 | 19.7 | 19.2 | Decomposition from 160° C |
| 5 | H₂N—CH₂—P(=O)(OH)(O⁻ NH₂⁺(CH₃)₂) | 1 | 16.1 | 16.1 | H₂O given off from 100° C; decomposition from 277° C |

-continued

| Ex. No. | Compound | Content of water of crystallisation (in moles) | Nitrogen content in % calculated | Nitrogen content in % found | Behaviour on heating |
|---|---|---|---|---|---|
| 6 | $H_2N-CH_2-\overset{O}{\underset{O^\ominus}{\overset{\|}{P}}}\overset{OH}{\underset{\overset{\oplus}{N}H_3CH(CH_3)_2}{}}$ | | | | Decomposition at 325° C |
| 7 | $H_2N-CH_2-\overset{O}{\underset{O^\ominus}{\overset{\|}{P}}}\overset{OH}{\underset{\overset{\oplus}{N}H_2(C_2H_5)_2}{}}$ | 0 | 15.2 | 14.7 | Decomposition from 275° C |
| 8 | $H_2N-CH_2-\overset{O}{\underset{O^\ominus}{\overset{\|}{P}}}\overset{OH}{\underset{H_2\overset{\oplus}{N}\text{(pyrrolidine)}}{}}$ | 1 | 14.0 | 14.4 | $H_2O$ given off from 100° C; decomposition from 185° C |
| 9 | $H_2N-CH_2-\overset{O}{\underset{O^\ominus}{\overset{\|}{P}}}\overset{OH}{\underset{H_2\overset{\oplus}{N}\text{(imidazole)}}{}}$ | 0 | 23.5 | 23.7 | Decomposition from 241° C |
| 10 | $H_2N-CH_2-\overset{O}{\underset{O^\ominus}{\overset{\|}{P}}}\overset{OH}{\underset{H_2\overset{\oplus}{N}\text{(morpholine)}}{}}$ | 0 | 14.1 | 14.0 | Decomposition from 265° C |
| 11 | $\left[H_2N-CH_2-\overset{O}{\underset{O^\ominus}{\overset{\|}{P}}}\overset{OH}{}\right]_2 H_3\overset{\oplus}{N}-CH_2-CH_2-\overset{\oplus}{N}H_3$ | 0 | 19.8 | 19.8 | Decomposition from 270° C (sinters beforehand) |
| 12 | $H_2N-CH_2-\overset{O}{\underset{O^\ominus}{\overset{\|}{P}}}\overset{OH}{\underset{\overset{\oplus}{N}H_3-C_4H_9}{}}$ | 2/3 | 14.2 | 14.2 | Decomposition from 322° C |
| 13 | $H_2N-CH_2-\overset{O}{\underset{O^\ominus}{\overset{\|}{P}}}\overset{OH}{\underset{\overset{\oplus}{N}H(C_2H_5)_3}{}}$ | 0 | 13.2 | 12.8 | Decomposition from 268° C |
| 14 | $H_2N-CH_2-\overset{O}{\underset{O^\ominus}{\overset{\|}{P}}}\overset{OH}{\underset{H_2\overset{\oplus}{N}\text{(piperidine)}}{}}$ | 0.5 | 13.6 | 13.5 | Decomposition from 182° C |
| 15 | $H_2N-CH_2-\overset{O}{\underset{O^\ominus}{\overset{\|}{P}}}\overset{OH}{\underset{H_3\overset{\oplus}{N}-CH_2-CO-O-C_2H_5}{}}$ | 0.5 | 12.5 | 12.5 | Decomposition from 254° C |
| 16 | $H_2N-CH_2-\overset{O}{\underset{O^\ominus}{\overset{\|}{P}}}\overset{OH}{\underset{H_3\overset{\oplus}{N}-CH_2-CH_2-OH}{}}$ | | | | Decomposition from 242° C |

EXAMPLE 17

Preparation of Calcium Aminomethanephosphonate

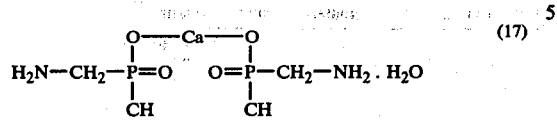
(17)

A solution of 8 g (0.2 mole) of sodium hydroxide in 40 ml of distilled water was added to a suspension of 22.22 g (0.2 mole) of aminomethanephosphonic acid in 100 ml of distilled water. A solution of 11.10 g (0.1 mole) of calcium chloride in 40 ml of distilled water was then added to the resulting clear solution of the monosodium salt of aminomethanephosphonic acid, while stirring. The precipitate which separated out was filtered off, washed with water and then dried. 27.8 g (100% of theory) of calcium aminomethanephosphonate, which did not melt on heating to 355° C, were thus obtained.

EXAMPLE 18

Preparation of Magnesium Aminomethanephosphonate

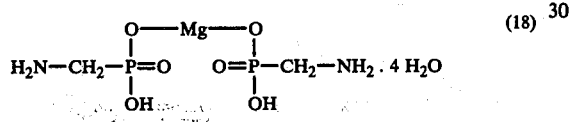
(18)

Magnesium aminomethanephosphonate was also obtained by a method of preparation analogous to that described in Example 17. Yield: 94% of theory.

On heating this salt, water was slowly released from 100° C onwards; from 264° C onwards, the substance decomposed with foaming.

EXAMPLE 19

Preparation of the Disodium Salt of Aminomethanephosphonic Acid

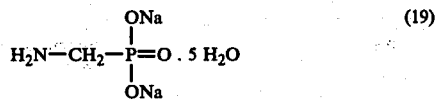
(19)

A solution of 8 g (0.2 mole) of sodium hydroxide in 40 ml of distilled water was added to a suspension of 11.11 g (0.1 mole) of aminomethanephosphonic acid in 50 ml of distilled water. Hereupon, salt formation occurred and a clear solution was formed. The solution was then evaporated to dryness in vacuo at a bath temperature of 70° C. The residue which hereupon remained was comminuted and left in vacuo at 70° C for a further 30 to 60 minutes. 24.15 (98.6% of theory) of the disodium salt of aminomethanephosphonic acid were thus obtained. On heating, the salt behaved as follows: at 84° to 85° C, liquefaction occurred, and from 124° C onwards the water of crystallization boiled off and the residue resolidified and did not melt again up to 355° C.

EXAMPLE 20

Preparation of Ammonium-Methyl-Phosphonic Acid Chloride

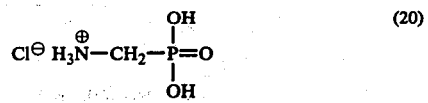
(20)

0.1 mole of hydrochloric acid was added to a suspension of 11.11 g (0.1 mole) of aminomethanephosphonic acid in 50 ml of distilled water. Hereupon salt formation occurred and a clear solution resulted. The solution was then evaporated to dryness in vacuo at a bath temperature of 70° C. The residue which hereupon remained was comminuted and was then left for a further 30 to 60 minutes in vacuo at 79° C. 14.6 g (99% of theory) of ammonium-methyl-phosphonic acid chloride of melting point 170°–172° C (decomposition) were thus obtained.

EXAMPLE 21

Preparation of Di-(ammonio-methyl-phosphonic acid) Sulfate

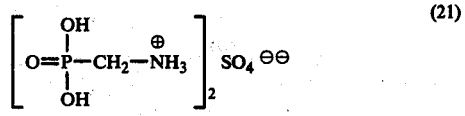
(21)

Di-(ammonio-methyl-phosphonic acid) sulfate was prepared, by a method analogous to the one described in Example 20, by reaction of aminomethanephosphonic acid with sulfuric acid. Di-(ammonio-methyl-phosphonic acid) sulfate of melting point 117°–119° C was thus obtained. Yield: 100% of theory.

The present invention also provides, as new compounds, aminomethanephosphonic acid derivatives of the formula

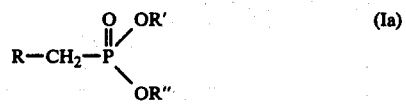
(Ia)

in which
R is an $NH_2$ group or an $-NH^{\oplus}_3 X^{\ominus}$ radical wherein $X^{\ominus}$ is one equivalent of an anion of an organic or inorganic acid, and R' and R'', which may be identical or different, are each one equivalent of an alkali metal or alkaline earth metal cation, one equivalent of a protonized nitrogen base or of a compound which contains an $N^{\oplus}H_3$ group, or hydrogen, provided that R' and R'' can simultaneously be hydrogen only if R is an $-N^{\oplus}H_3 X^{\ominus}$ radical.

The active compounds to be used according to the invention affect the physiological metabolism of plant growth and can therefore be used as plant-growth regulators.

The diverse effects of the active compounds depend essentially on the point in time at which they are used, relative to the stage of development of the seed or of the plant, and on the concentrations used.

Plant-growth regulators are used for various purposes which are related to the stage of development of the plant.

The growth of the plant can be greatly inhibited by means of the compounds according to the invention. This inhibition of growth is of interest in the case of grasses in order to reduce the frequency with which the grass has to be cut. An inhibition of vegetative growth also plays an important role in cereals since this can reduce or completely prevent falling-over.

In the case of many crop plants, inhibition of the vegetative growth permits denser planting of the crop so that an increased yield relative to soil area can be achieved. A further mechanism of increasing the yield by means of growth inhibitors is based on the fact that the nutrients benefit blossoming and fruiting to an increased extent while vegetative growth is restricted.

The active compounds to be used according to the present invention can be converted into the usual formulations, such as solutions, emulsions, suspensions, powders, pastes and granulates. There may be produced in known manner, for example by mixing the active compounds with extenders, that is, liquid or solid or liquefied gaseous diluents or carriers, optionally with the use of surface-active agents, that is, emulsifying agents and/or dispersing agents and/or foam-forming agents. In the case of the use of water as an extender, organic solvents can, for example, also be used as auxiliary solvents.

As liquid diluents or carriers, there are preferably used aromatic hydrocarbons, such as xylenes, toluene, benzene or alkyl naphthalenes, chlorinated aromatic or aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethyl formamide, dimethyl sulfoxide or acetonitrile, as well as water.

By liquefied gaseous diluents or carriers are meant liquids which would be gaseous at normal temperatures and pressures, for example aerosol propellants, such as halogenated hydrocarbons, for example freon.

As solid diluents or carriers, there are preferably used ground natural minerals, such as kaolins, clays, talc, chalk, quartz, attapulgite, montmorillonite or diatomaceous earth, or ground synthetic minerals, such as highly-dispersed silicic acid, alumina or silicates.

Preferred examples of emulsifying and foam-forming agents include non-ionic and anionic emulsifiers, such as polyoxyethylene-fatty acid esters, polyoxyethylene-fatty alcohol ethers, for example alkylarylpolyglycol ethers, alkyl sulfonates, alkyl sulfates and aryl sulfonates as well as albumin hydrolyzation products; and preferred examples of dispersing agents include lignin sulfite waste liquors and methyl cellulose.

The active compounds to be used according to the invention can be present in the formulations as a mixture with other active compounds.

The formulations in general contain from 0.1 to 95 percent by weight of active compound, preferably from 0.5 to 90 percent.

The active compounds can be used as such, as their formulations or as the application forms prepared therefrom, such as ready-to-use solutions, emulsions, foams, suspensions, powders, pastes and granules. They may be used in the customary manner, for example by watering, spraying, atomizing, dusting, scattering and the like.

The concentrations of active compound in the ready-to-use formulations can be varied within a fairly wide range. In general, concentrations from 0.0005 to 2%, preferably from 0.01 to 0.5% by weight, are used.

Furthermore, 0.01 to 20 kg, preferably 0.1 to 10 kg, of active compound are, in general, used per hectare of soil area.

The preferred period of time within which the growth regulators are used depends on the climatic and vegetative circumstances.

The present invention further provides plants the growth of which has been regulated by their being grown in areas in which immediately prior to and/or during the time of the growing of a compound of the formula (I) above was applied alone or in admixture with a diluent or carrier. It will be seen that the usual methods of providing a harvested crop may be improved by the present invention.

In the test Examples which follow, the activity as growth regulators of the compounds to be used according to the invention is illustrated, without excluding the possibility of further uses as growth regulators.

EXAMPLE A

Inhibition of growth/wheat
Solvent: 10 parts by weight of methanol
Emulsifier: 2 parts by weight of polyethylene sorbitan monolaurate.

To prepare a suitable preparation of active compound, one part by weight of active compound was mixed with the stated amount of solvent and emulsifier and the mixture was made up to the desired concentration with water.

Young wheat plants, 25 cm high, were sprayed with the preparation of active compound until dripping wet. After 4 weeks, the additional growth was measured and the inhibition of growth in % of the additional growth of the control plants was calculated. 100% means that growth had stopped and 0% denotes a growth corresponding to that of the untreated plants.

The active compounds, active-compound concentrations and results can be seen from Table A which follows.

Table A

| Active compound | Concentration in ppm | Inhibition of growth in % of the control |
|---|---|---|
| Water (control) | — | 0 |
| $Cl-CH_2-CH_2-\overset{\oplus}{N}(CH_3)_3 \; Cl^{\ominus}$ (known) | 500 | 60 |
| (1) $H_2N-CH_2-\overset{O}{\underset{\|}{P}}\begin{matrix}OH\\ONa\end{matrix}$ | 500 | 80 |
| (3) $H_2N-CH_2-\overset{O}{\underset{\|}{P}}\begin{matrix}OH\\ONH_4\end{matrix}$ | 500 | 100 |
| (16) $H_2N-CH_2-\overset{O}{\underset{\|}{P}}\begin{matrix}OH\\O^{\ominus} \; H_3\overset{\oplus}{N}-CH_2-CH_2-OH\end{matrix}$ | 500 | 85 |

Table A-continued

Inhibition of growth/wheat

| Active compound | Concentration in ppm | Inhibition of growth in % of the control |
|---|---|---|
| (6) $H_2N-CH_2-\underset{\underset{O^{\ominus}\ \overset{\oplus}{N}H_3-CH(CH_3)_2}{\|}}{\overset{O}{\overset{\|}{P}}}\!\!\diagup\!\!^{OH}$ | 500 | 80 |

EXAMPLE B

Inhibition of growth/barley
Solvent: 10 parts by weight of methanol
Emulsifier: 2 parts by weight of polyethylene sorbitan monolaurate.

To prepare a suitable preparation of active compound, one part by weight of active compound was mixed with the stated amount of solvent and emulsifier and the mixture was made up to the desired concentration with water.

Young barley plants, 25 cm high, were sprayed with the preparation of active compound until dripping wet. After 4 weeks, the additional growth was measured and the inhibition of growth in % of the additional growth of the control plants was calculated. 100% means that growth had stopped and 0% denotes a growth corresponding to that of the untreated plants.

The active compound, active-compound concentrations and results can be seen from Table B which follows.

Table B

Inhibition of growth/barley

| Active compound | Concentration in ppm | Inhibition of growth in % of the control |
|---|---|---|
| Water (control) | — | 0 |
| $ClCH_2-CH_2-\overset{\oplus}{N}(CH_3)_3\ Cl^{\ominus}$ (known) | 500 | 35 |

Table B-continued

Inhibition of growth/barley

| Active compound | Concentration in ppm | Inhibition of growth in % of the control |
|---|---|---|
| (1) $H_2N-CH_2-\overset{O}{\underset{\|}{P}}\!\!\diagdown\!\!\diagup\!\!^{OH}_{ONa}$ | 500 | 75 |
| (3) $H_2N-CH_2-\overset{O}{\underset{\|}{P}}\!\!\diagdown\!\!\diagup\!\!^{OH}_{ONH_4}$ | 500 | 45 |
| (16) $H_2N-CH_2-\overset{O}{\underset{\|}{P}}\!\!\diagdown\!\!\diagup\!\!^{OH}_{O^{\ominus}\ \overset{\oplus}{H_3N}-CH_2-CH_2-OH}$ | 500 | 90 |
| (6) $H_2N-CH_2-\overset{O}{\underset{\|}{P}}\!\!\diagdown\!\!\diagup\!\!^{OH}_{O^{\ominus}\ \overset{\oplus}{N}H_3-CH(CH_3)_2}$ | 500 | 80 |

It will be understood that the specification and examples are illustrative but not limitative of the present invention and that other embodiments within the spirit and scope of the invention will suggest themselves to those skilled in the art.

What is claimed is:

1. Method of inhibiting the growth of cereal crops which method comprises applying to the plants or their habitat effective amounts of an aminomethanephosphonic acid compound of the formula

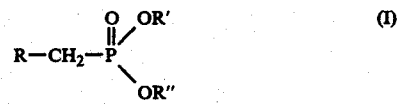

in which
R is an $-NH^{\oplus}_3 X^{\ominus}$ radical wherein
$X^{\ominus}$ is one equivalent of a chloride anion or sulfate, and
R' and R" are both hydrogen.

2. Method as claimed in claim 1 wherein said compound is used to inhibit the growth of wheat plants.

3. Method as claimed in claim 1 wherein said compound is used to inhibit the growth of barley plants.

* * * * *

UNITED STATES PATENT AND TRADEMARK OFFICE
CERTIFICATE OF CORRECTION

PATENT NO. : 4,127,401
DATED : November 28, 1978
INVENTOR(S) : COLIN et al.

It is certified that error appears in the above-identified patent and that said Letters Patent are hereby corrected as shown below:

Column 6, Example 8, last column, "100°C" should read

-- 140°C --.

Column 8, line 18, "79°" should read -- 70° --.

Signed and Sealed this

Third Day of April 1979

[SEAL]

Attest:

RUTH C. MASON
Attesting Officer

DONALD W. BANNER
Commissioner of Patents and Trademarks